United States Patent [19]
Kortenoeven-van den Beuken et al.

[11] 3,991,128
[45] Nov. 9, 1976

[54] PROCESS FOR THE PRODUCTION OF VINYLPYRENES

[75] Inventors: Johanna L. E. Kortenoeven-van den Beuken, Helden-Panningen; Gerardus J. Crommentuyn, Lottum, both of Netherlands

[73] Assignee: Oce-van der Grinten N.V., Venlo, Netherlands

[22] Filed: Sept. 26, 1975

[21] Appl. No.: 617,012

[30] Foreign Application Priority Data

Oct. 11, 1974 United Kingdom............... 44236/74

[52] U.S. Cl. .................... 260/669 QZ; 260/668 D; 260/668 F
[51] Int. Cl.²......................................... C07C 15/36
[58] Field of Search ............ 260/668 D, 668 F, 669

[56] References Cited
OTHER PUBLICATIONS

W. E. Bachmann et al., J. Amer. Chem. Soc., 63, pp. 2494–2499, 1941.
Ralph G. Flowers et al., J. Amer. Chem. Soc., 71, p. 3104, 1949.

Primary Examiner—Veronica O'Keefe
Attorney, Agent, or Firm—Albert C. Johnston

[57] ABSTRACT

Vinylpyrene (substituted or not) is prepared in a single reaction stage by reacting the corresponding acetylpyrene with a metal alkoxide, e.g. aluminum isopropoxide, in an inert organic solvent, e.g. a xylene, at a temperature above 110° C. which, for some reaction conditions, optimally is between 130° and 150° C. The presence of hydroquinone in the mixture reduces the time and increases the yield of the reaction.

8 Claims, No Drawings

PROCESS FOR THE PRODUCTION OF VINYLPYRENES

This invention relates to a process for the production of vinylpyrenes from the corresponding acetylpyrenes.

According to the present invention, there is provided a process for preparing a substituted or unsubstituted vinylpyrene, which process comprises reacting the corresponding acetylpyrene with a metal alkoxide in an inert organic solvent at a temperature above 110° C; and separating the vinylpyrene so formed from the reaction mixture.

In the Journal of the Americal Chemical Society 71 (1949) page 3104 there is disclosed a process whereby 1-vinylpyrene can be prepared from 1-acetylpyrene in two steps. The first step comprises the production of 1-(α-hydroxyethyl)-pyrene by reducing 1-acetylpyrene with hydrogen in the presence of a copper- chromium oxide catalyst. In the second step the 1-(α-hydroxyethyl)-pyrene is converted into 1-vinylpyrene by passing through a column packed with alumina pellets. In the Journal of the American Chemical Society 63 (1941) page 2495 there is disclosed a process whereby 1-(α-hydroxyethyl)-pyrene may also be prepared by reacting 1-acetylpyrene with aluminum isopropoxide in isopropanol. These two-step processes have the disadvantages that the second step is very time consuming; needs expensive equipment if performed on a large scale; and results in the very low yield of about 15%.

It has now been found that the two-step conversion of acetylpyrene proceeds in one and the same reaction mixture if the reaction with a metal alkoxide is performed at a temperature above 110° C. In the known process 1-acetylpyrene is reacted with aluminium isopropoxide in isopropanol and as a consequence the reaction temperature cannot be raised above about 82° C, which is the boiling temperature of isopropanol.

Besides vinylpyrene, substituted vinylpyrenes such as bromo vinylpyrene can be prepared from the corresponding acetylpyrene by applying the process according to the invention. A great number of metal alkoxides which can be used in the process according to the invention is commercially available. For example ethoxides, isopropoxides and sec.-butoxides of metals such as sodium, magnesium, aluminium, tin and zirconium may be used as far as they dissolve in the inert solvent selected for the reaction, but the best results are obtained with aluminium isopropoxide. The inert solvent may be a common organic solvent boiling above 110° C as far as it is not attacked by the metal alkoxide. Usually, ortho-, meta- or para-xylene or a mixture thereof is quite satisfactory, but other hydrocarbons such as aliphatic hydrocarbon fractions boiling between 110° and 200° C, toluene, ethylbenzene and cumene and ethers such as di-n-butyl ether may also be used. Ketones and esters are usually less suitable for the present purpose as many of these products react with the metal alkoxide.

The reaction temperature is not critical as far as it is maintained above 110° C, but preferably the temperature is maintained between 130° and 150° C. At temperatures below 130° C the reaction time must be increased and at temperatures above 150° C the yield is lower as a result of uncontrolled thermal polymerisation of the vinylpyrene formed. The reaction time required for an optimal yield depends on the reaction conditions. If the reaction is performed with aluminium isopropoxide in boiling m-xylene, a reaction time of about 2 hours is required for a yield of about 50%. Surprisingly it was possible to decrease the reaction time to 1 hour by adding hydroquinone to the mixture of starting materials. In this case the yield of the reaction with aluminium isopropoxide in boiling m-xylene was about 60%.

EXAMPLE I

A mixture of
12 g 1-acetylpyrene
11 g aluminum isopropoxide
0.05 g hydroquinone, and
80 ml m-xylene was refluxed. During the reaction, which was completed within 1 hour, acetone was continuously distilled from the reaction mixture. The reaction mixture was washed three times, two times with 75 $cm^3$ of a solution containing 100 g of sodiumhydroxide per liter and once with water. After each washing step the aqueous phase was separated from the non-aqueous phase consisting of a solution of vinylpyrene in m-xylene. The vinylpyrene solution was dried over sodium sulphate and concentrated by distilling under vacuum. The resulting vinylpyrene was dissolved in hot ethanol, the hot solution was filtered over charcoal and 6 g of yellowish crystalline 1-vinylpyrene with a melting point of 85° – 87° C were precipitated from the solution by cooling.

EXAMPLE II

A mixture of
12 g 1-acetylpyrene
13.3 g aluminum butoxide
0.05 g hydroquinone, and
80 ml m-xylene was heated in the same manner as described by Example I. The result was 3 g of yellowish crystalline 1-vinylpyrene with a melting point of 85°–87° C.

What we claim is:

1. A process for preparing a vinylpyrene, which process comprises reacting an unsubstituted or bromo-substituted acetylpyrene with a $C_1$ to $C_4$ alkoxide of a metal selected from the group consisting of sodium, magnesium, aluminum, tin, or zirconium in an inert organic solvent at a temperature above 110° C; and separating the vinylpyrene so formed from the reaction mixture.

2. A process according to claim 1 wherein the acetylpyrene is a 1-acetylpyrene.

3. A process according to claim 1 wherein the metal alkoxide is an aluminum alkoxide.

4. A process according to claim 1 wherein the metal alkoxide is aluminum isopropoxide.

5. A process according to claim 1 wherein the reaction is performed at a temperature between 130° and 150° C.

6. A process according to claim 1 wherein the inert organic solvent is m-xylene.

7. A process according to claim 1 wherein the reaction is performed in the presence of hydroquinone.

8. A process for preparing 1-vinylpyrene, which process comprises reacting 1-acetylpyrene with aluminum isopropoxide in the presence of hydroquinone, in a xylene solvent at a temperature between 130° and 150° C., and separating the 1-vinylpyrene so formed from the reaction mixture.

* * * * *